(12) United States Patent
Teves et al.

(10) Patent No.: US 6,820,622 B1
(45) Date of Patent: Nov. 23, 2004

(54) THERMAL SURGICAL DRAPE

(76) Inventors: Leonides Y. Teves, 1607 54th St. West, Bradenton, FL (US) 34209; Steven D. McCarus, 10815 Boca Pointe Dr., Orlando, FL (US) 32836-5861

( * ) Notice: Subject to any disclaimer, the term of this patent is extended or adjusted under 35 U.S.C. 154(b) by 326 days.

(21) Appl. No.: 10/064,076

(22) Filed: Jun. 7, 2002

(51) Int. Cl.[7] .............................................. A61B 19/00
(52) U.S. Cl. ...................... 128/849; 128/853; 128/854; 2/458
(58) Field of Search ................................ 128/849, 853, 128/854, 852, 857; 2/458, 88, DIG. 3, DIG. 5; 219/212

(56) References Cited

U.S. PATENT DOCUMENTS

| | | | | |
|---|---|---|---|---|
| 4,889,136 A | * | 12/1989 | Hanssen | 128/853 |
| RE34,816 E | * | 1/1995 | Poettgen | 128/849 |
| 5,546,960 A | * | 8/1996 | Billgren | 128/849 |
| 5,797,402 A | * | 8/1998 | West | 128/849 |
| 5,901,706 A | * | 5/1999 | Griesbach et al. | 128/849 |
| 5,947,122 A | * | 9/1999 | McDonald et al. | 128/849 |
| 6,167,885 B1 | * | 1/2001 | Hanssen | 128/849 |
| 6,564,803 B2 | * | 5/2003 | Lofgren | 128/849 |
| 6,615,837 B1 | * | 9/2003 | Griesbach, III | 128/849 |

* cited by examiner

*Primary Examiner*—Fadi H. Dahbour
(74) *Attorney, Agent, or Firm*—Ronald E. Smith; Smith & Hopen, P.A.

(57) ABSTRACT

A combination surgical drape and blanket covers the entire body of a supine patient to provide draping and body temperature management in a single structure. A flexible sheet of plastic overlies a flexible substrate and is connected to the substrate at its periphery to create a hollow space into which warm air is pumped. A plurality of tie-downs maintains a low profile for the inflated cover. Removable panels grant access to areas of the body for surgical procedures. The structure includes a tool-holding platform and a releasably mounted urine drainage system that enables a patient to remain connected to a urine drainage bag even when the combination surgical drape and blanket is removed at the conclusion of a surgical procedure.

6 Claims, 7 Drawing Sheets

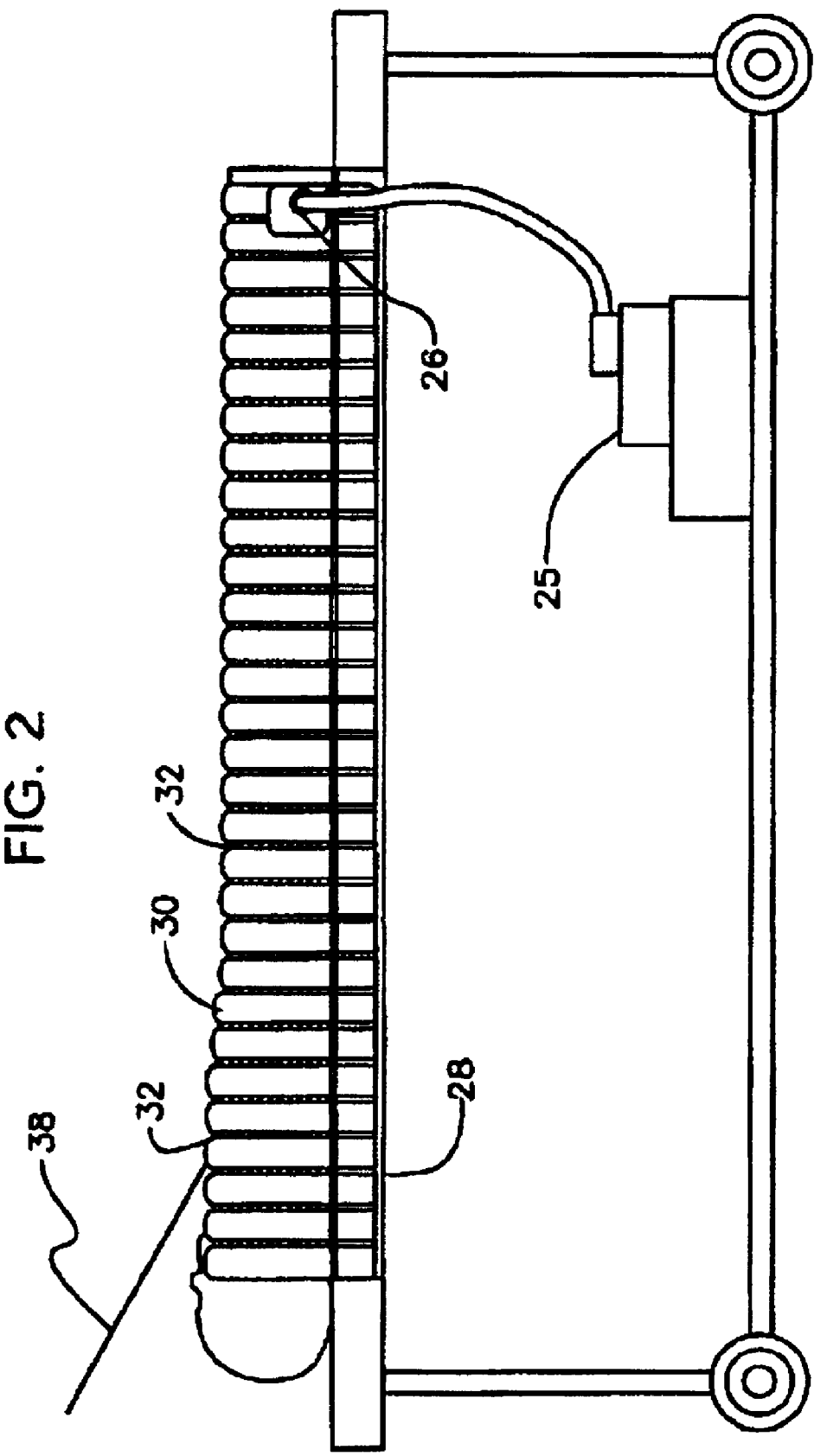

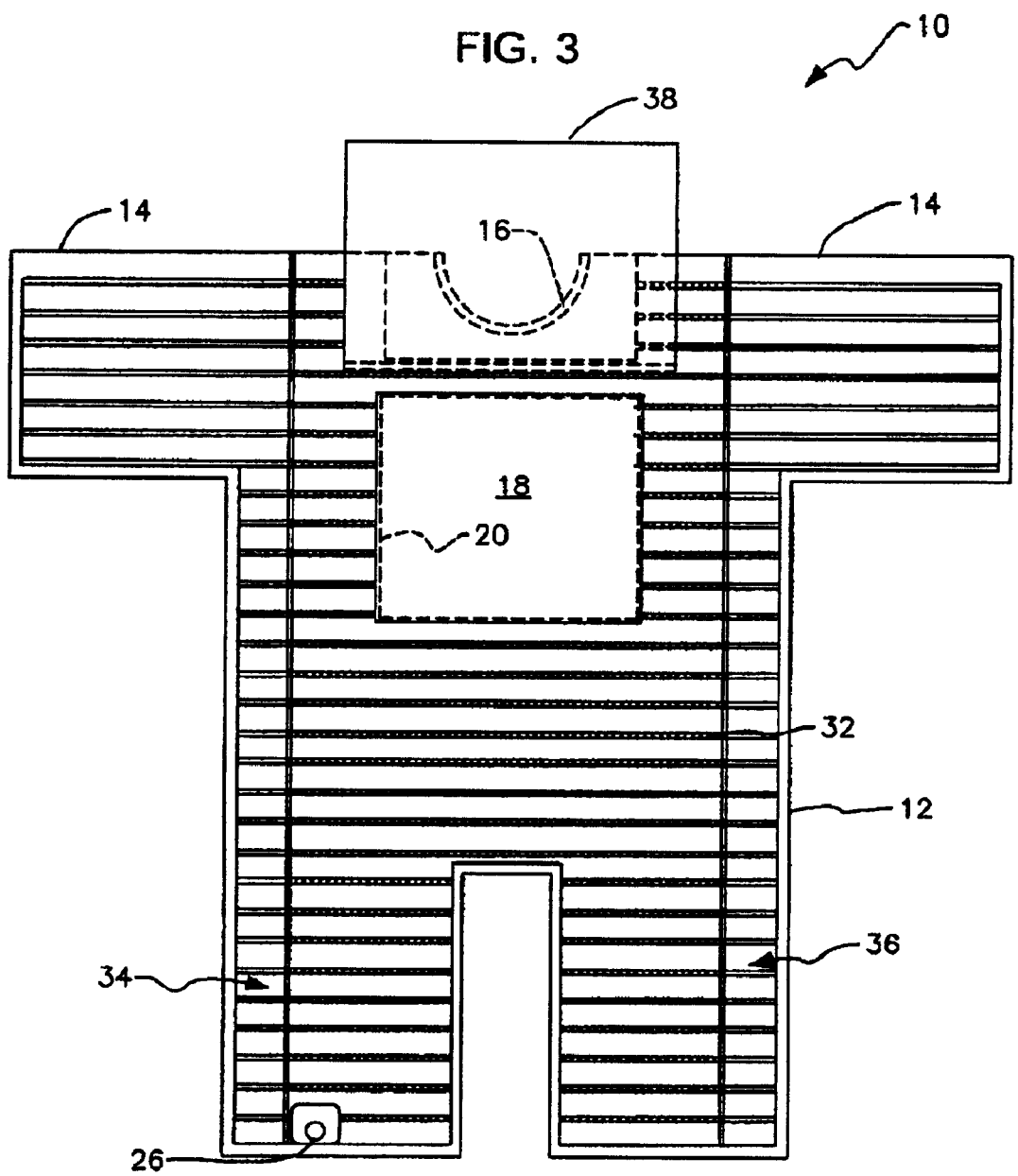

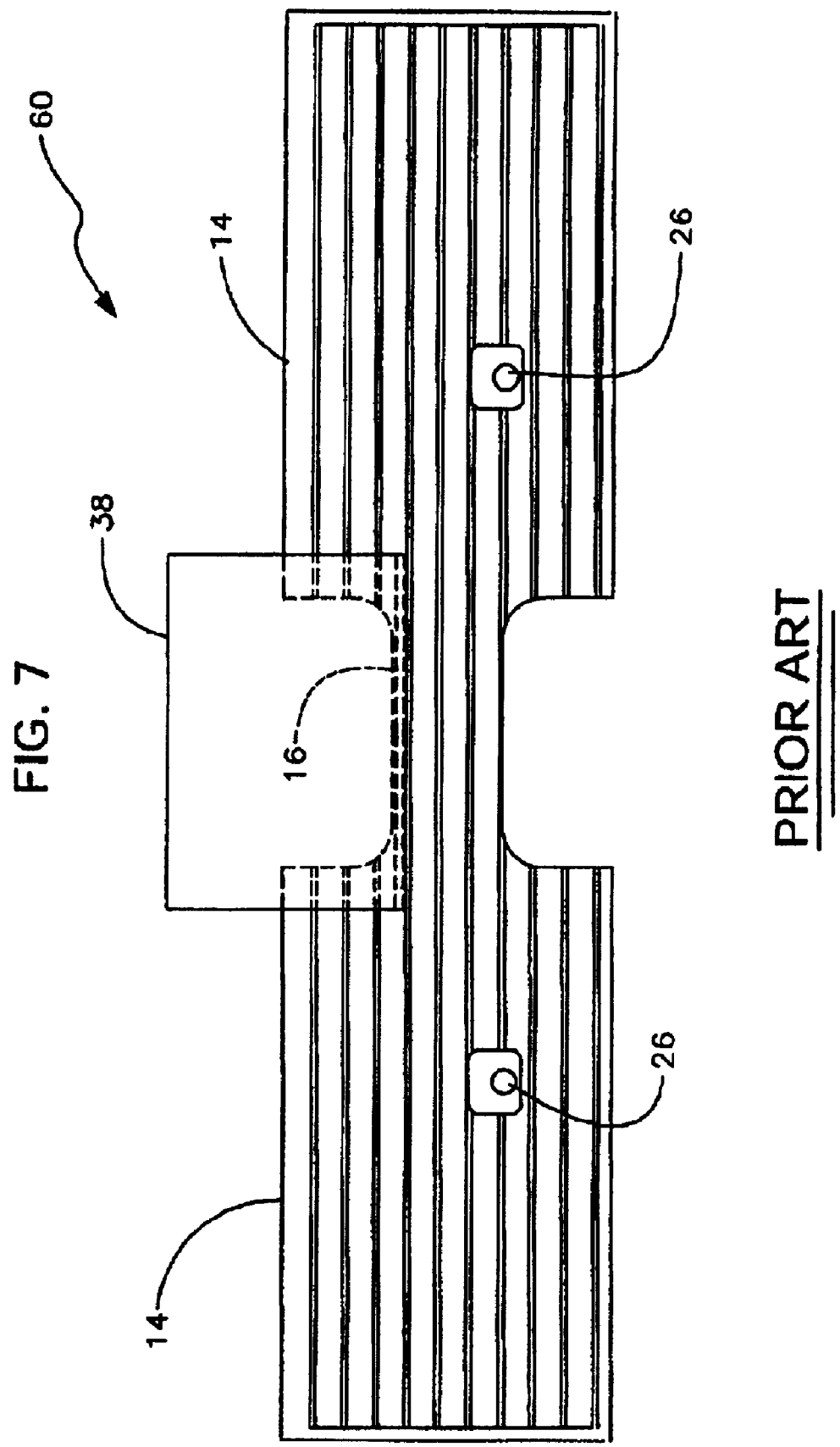

THERMAL SURGICAL DRAPE

BACKGROUND OF INVENTION

1. Field of the Invention

This invention relates, generally, to medical appliances. More particularly, it relates to means and methods for avoiding hypothermic conditions in a patient undergoing surgery.

2. Description of the Prior Art

Surgical procedures are typically performed in operating rooms where the temperature is maintained at about sixty three degrees Fahrenheit (63° F.) to inhibit the growth of bacterial infections. Although the medical staff can dress appropriately for the cool temperature, the patient is usually in a state of undress and can experience hypothermia if not provided with a warming means. Surgical drapes are not intended to and do not function as a warming means. A conventional blanket can do the job, but it is not cost effective to sterilize and re-use blankets or to purchase a new blanket for each surgical procedure.

Accordingly, inventors have developed light-in-weight, disposable articles that perform the function of a conventional blanket. One popular blanket means is sold under the trademark Bair Hugger® blanket. It performs patient temperature management by distributing warm air from a blower means throughout a structure that looks something like a swimming pool raft when inflated. It is placed in transverse relation to a supine patient so that its main body or medial part covers and warms the patients chest area and its opposite ends cover the patient's outstretched arms. The abdomen and legs of the patient are not covered. Thus, the blanket does not serve as a surgical drape.

The conventional use of surgical drapes and blanket means results in the patient being billed for both items. It would therefore be highly advantageous and more economical from a patient's perspective if a structure could be provided that combined the respective functions of surgical drapes and blanket means.

The Bair Hugger® blanket and others like it also provide a rectangular plastic shield that covers the patient's face. One end of the shield is attached to the blanket means in the upper chest region thereof and the two corners of the free end of the shield are tied to upstanding poles positioned on opposite sides of the head of the operating table, such poles typically being used to support items such as intravenous feeding bottles. The shield protects the patient's face from dropped surgical instruments and the like.

There are numerous times throughout the course of an operation where a surgeon needs to lay one tool down and to pick up another. Having an assistant take the relinquished tool and supply the new tool is burdensome on both the surgeon and the assistant. The above-mentioned plastic shield is positioned at an angle relative to a horizontal plane and therefore cannot be used to deposit tools thereupon. Thus, a platform for the support of such tools would be desirable.

One drawback of the known blanket means is that they are quite thick when inflated with warm air. Their bulk can interfere with the movements of the surgical team. Thus, a blanket that is less bulky when inflated and that does not sacrifice patient temperature control would overcome that particular shortcoming.

One member of the surgical team, the anesthesiologist, monitors the urine output of the patient during surgery, among other duties. In most cases, a Foley® catheter or equivalent connects the patient's bladder to an elongate tube that extends from the foot of the operating table to the head thereof where the urine collection bag is positioned for the convenience of the anesthesiologist. When conventional surgical drapes and blanket means are used, no provision is made for accommodation of the Foley® catheter or the elongate tube. The Foley® catheter must therefore be disconnected from the patient and from the elongate tube when the operation is over so that the patient can be taken to the recovery room. In some cases, the Foley® catheter must then be reinserted into the bladder and the elongate tube reconnected. Thus, a blanket means that would enable a patient to remain attached to the Foley® catheter even after removal of the blanket means at the conclusion of a surgical procedure would be highly advantageous.

However, in view of the prior art considered as a whole at the time the present invention was made, it was not obvious to those of ordinary skill in the pertinent art how the perceived needs could be fulfilled.

SUMMARY OF INVENTION

The long-standing but heretofore unfulfilled need for a combination surgical drape and blanket means for patient temperature management is met by a construction that includes a substrate formed of a flexible material having a main body adapted to overlie a patient. The substrate has a width and length sufficient to cover the shoulders, chest, torso, and legs of a patient, and it includes a pair of arm-covering members connected to and extending from the main body on opposite sides thereof. A flexible sheet of material overlies the main body and the arm-covering members. A plurality of interconnecting members interconnect the substrate and the flexible sheet of material. Each interconnecting member joins the substrate and the flexible sheet of material together at a point so that the substrate and flexible sheet of material are unconnected to one another around that point. An air inlet admits air into a space between the substrate and the flexible sheet of material. The air inlet is adapted to admit warm compressed air from a remote source of warm compressed air into the space between the substrate and the flexible sheet of material. A plurality of small vent holes are formed in the flexible sheet of material to enable warm compressed air in the space to flow therefrom.

A removably mounted panel is formed in the main body and includes a section of substrate and flexible sheet of material bonded to one another at a peripheral edge of the panel so that the panel is not in fluid communication with the inlet means so that when the removable panel is removed, compressed warm air continues to flow throughout the arm-covering members and all parts of the main body outside the boundary of the removable panel.

The combination surgical drape and blanket performs the function of a surgical drape when disposed in overlying relation to patient, and performs the function of a blanket when warm compressed air is admitted into the space. Removal of the removable panel exposes a part of the patient's body to which access is needed for a surgical procedure.

A concavity adapted to receive a patient's head is formed in the main body in a transversely disposed edge thereof. A flexible shield of rectangular construction is connected at a first edge to the main body just below that concavity, i.e., at the upper chest area, and has a second edge opposite to the first edge adapted to be connected to a support means at a point above the patient's head so that the shield is disposed at an angle over the patient's head. A rigid platform member is disposed in overlying relation to the flexible shield and at least one clamp is secured to the platform. The at least one clamp is adapted to hold a tool deposited atop the platform. A tool deposited atop the platform therefore does not roll down the platform so that it is available for use at any time. The at least one clamp includes at least one pair of laterally spaced apart clamps so that a first end of a tool is supported by a first clamp and so that a second end of the tool is supported by a second clamp. Each clamp of each pair of laterally spaced apart clamps is hingedly mounted to the rigid platform so that it is storable atop the rigid platform in a folded configuration when not in use and is positioned in upstanding relation to the rigid platform when disposed in an operable configuration.

In a further embodiment, a pair of bifurcated leg-covering members extend from the main body. Each leg member has a structure like that of the main body and the arm-covering members so that the legs of the patient are individually covered and draped.

The combination surgical drape and blanket further includes an elongate tube and a plurality of support blocks arranged along the length of the elongate tube at predetermined intervals. Each of the support blocks is adapted to receive the elongate tube therethrough. Each of the support blocks is detachably secured to a peripheral edge of the combination surgical drape and blanket.

A first connector means adapted for releasable engagement with a distal end of a urine drainage catheter is disposed at a first end of the elongate tube. A second connector means adapted for releasable engagement with a urine collection bag is disposed at a second end of the elongate tube. In this way, when a surgical procedure has been completed, each of the support blocks is separated from the combination surgical drape and blanket so that the first and second connector means remain connected to the urine drainage catheter and said urine collection bag, respectively. The combination thermal blanket and surgical drape is then removed from covering relation to the patient. This avoids having to disconnect the urine collection assembly when the combination thermal blanket and surgical drape is removed and having to reconnect said urine collection assembly when the patient is brought to the recovery room.

An important object of this invention is to provide a surgical blanket and a surgical drape as an integrated, single item.

Another important object is to provide a combination surgical blanket and drape that covers the entire body of a patient to protect the entire body from hypothermia.

Another important object is to provide a combination blanket and drape that remains in a relatively thin condition when fully inflated.

Still another object is to provide a combination blanket and drape having a removable access panel in the chest area thereof so that the panel may be removed for surgical procedures in the chest area of the patient.

Still another object is to provide a combination blanket and drape having a removable access panel in the abdominal area thereof so that said panel may be removed for surgical procedures in the abdominal area of the patient.

Another object is to provide a combination blanket and drape having means for holding tools used during surgery.

Another major object is to provide a combination blanket and drape that enables a patient connected to a urine collection bag to remain connected to said bag even after a surgical procedure has concluded and the novel combination blanket and drape have been removed.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 2 is a side elevational view of the thermal surgical drape connected to a source of warm compressed air;

FIG. 3 is a top plan view of a second embodiment having a bifurcated lower section;

FIG. 7 is a top plan view of a prior art surgical drape.

DETAILED DESCRIPTION

Figure 1A:
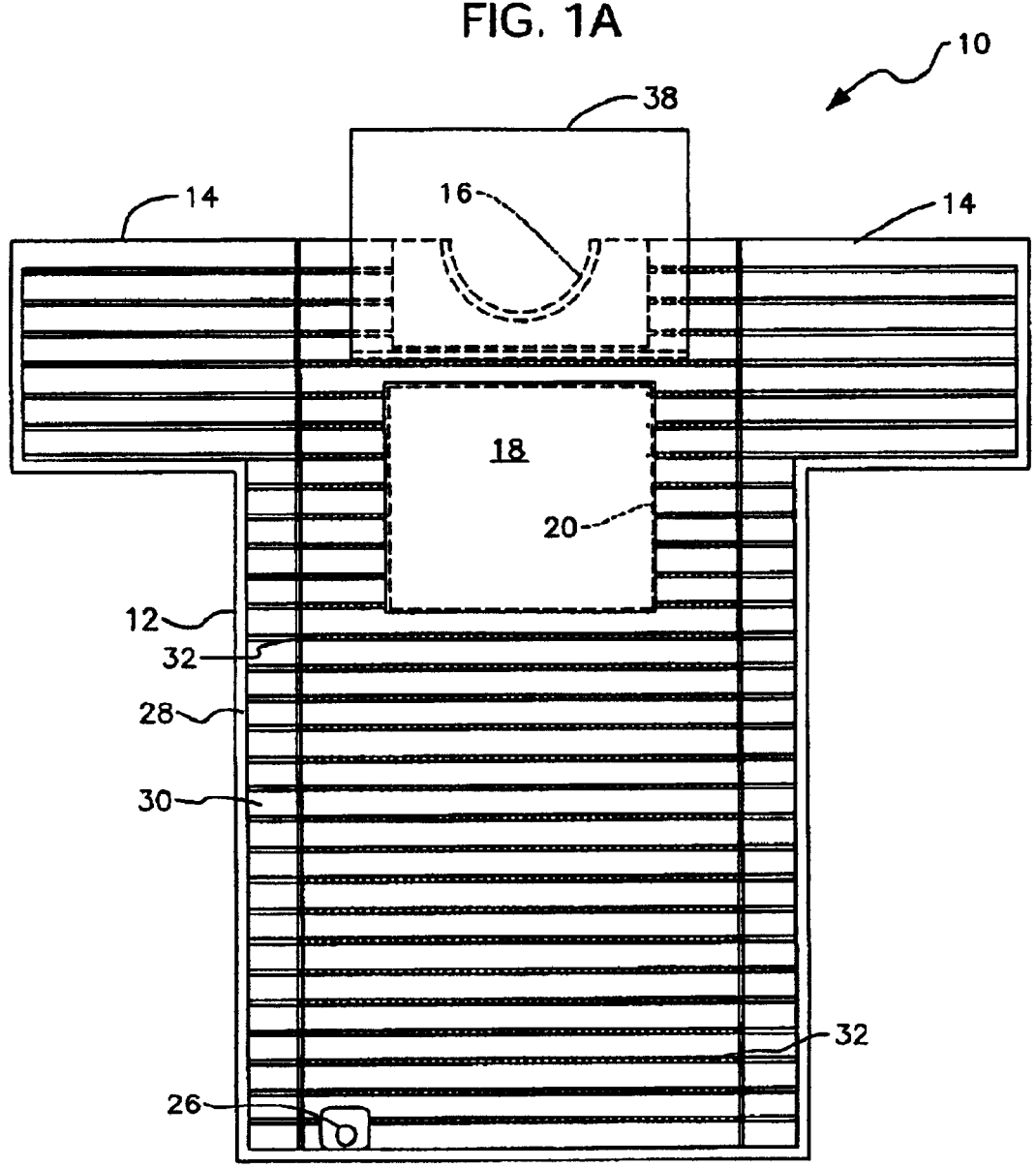
FIG. 1A is a top plan view of a first embodiment of the novel thermal surgical drape.
Figure 1B:
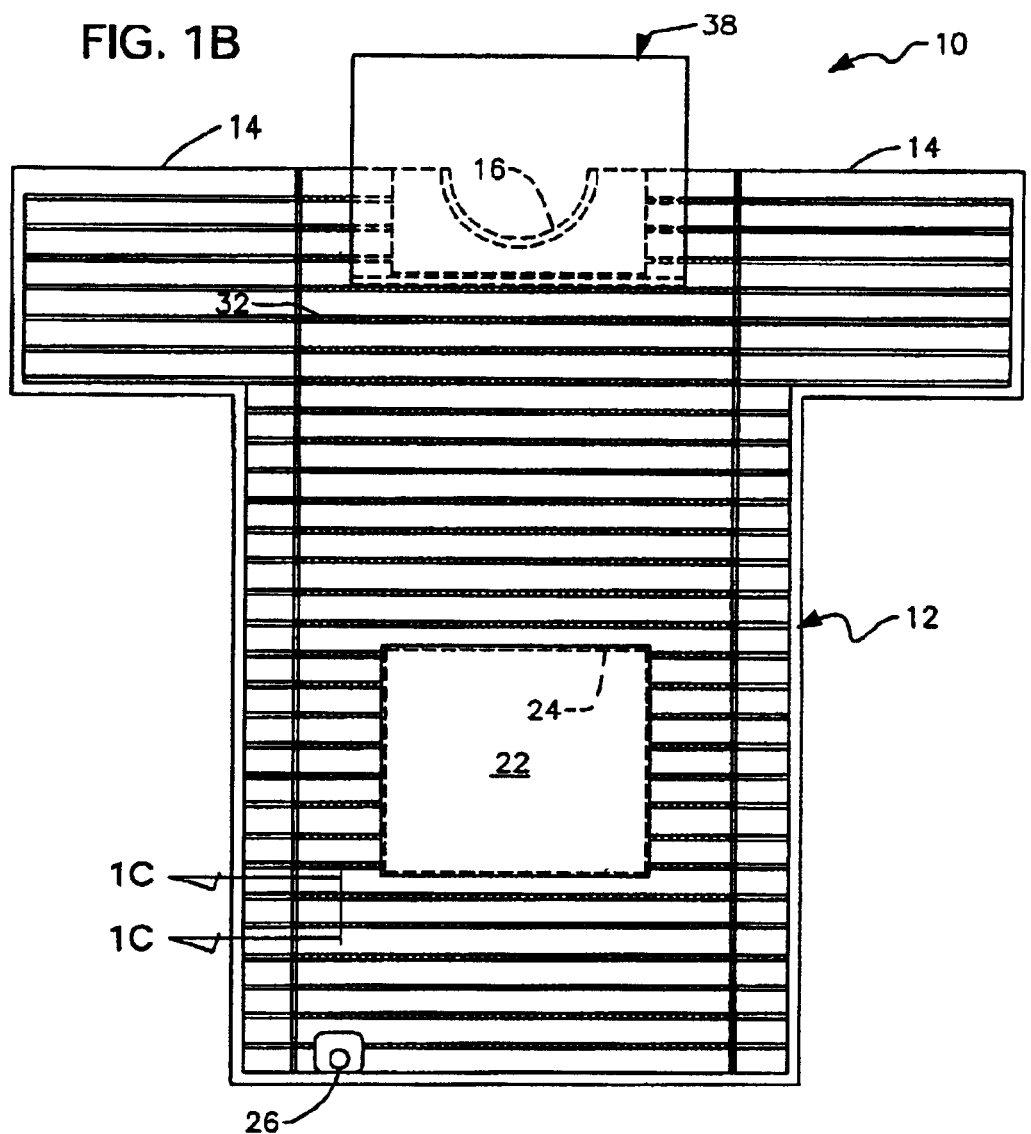
FIG. 1B is a top plan view of an alternative of the first embodiment.
Figure 1C:
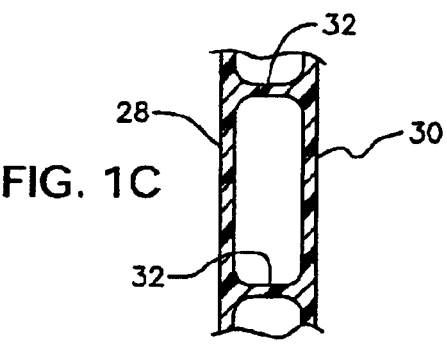
FIG. 1C is a sectional view taken along line 1C—1C in FIG. 1B.

Referring to FIGS. 1A, 1B, and 1C, it will there be seen that the reference numeral 10 denotes an illustrative embodiment of the novel thermal surgical drape as a whole. The rectangular structure of main body 12 enables it to overlie a patient from neck to toe. Transversely disposed arms 14, 14 overlie a patient's outstretched arms. Concavity 16 accommodates a patient's head.

If a procedure is to be performed in the chest area, panel 18 is removed to expose that region of the patient's body. Perforations 20 are formed in the border of panel 18 to facilitate removal of said panel. If a procedure is to be performed in the abdominal, inguinal, or lower extremities, panel 22 (FIG. 1B) is removed. Perforations 24 facilitate the removal of panel 22.

As best understood in connection with FIG. 2, warm air from a source 25 of compressed warm air is introduced into thermal surgical drape 10 at air inlet 26. Specifically, as best understood in connection with FIG. 1C, the warm air under pressure is introduced above the waterproof, thermal insulation part or substrate 28 and below flexible plastic sheet 30 so that said sheet is elevated as depicted relative to substrate 28 when the warm air is introduced. Substrate 28 has a high coefficient of thermal conductivity so that the warmth provided by the circulating warm air is efficiently transferred to the patient.

To prevent thermal surgical drape 10 from becoming bulky when inflated, a plurality of buttons or tie-downs, collectively denoted 32, are positioned throughout thermal surgical drape 10 in interconnecting relation to substrate 28 and plastic sheet 30. In this way, warm air circulates over all parts of substrate 28 and warms the patient. A plurality of small exhaust openings, not shown, enable the warm air to escape into the environment, thereby enabling circulation of warm air between said thermal insulation part 28 and said plastic sheet 30.

The area occupied by chest panel 18 (FIG. 1A) or lower panel 22 (FIG. 1B) is not in fluid communication with air inlet 26. Said removable panels are sealed about their respective peripheries. Specifically, the seals are outward of the aforementioned perforations so that said seals are unaffected when a panel is removed.

In a first commercial embodiment, thermal surgical drape 10 would include removable chest panel 18 as in FIG. 1A but not removable panel 22 as n FIG. 1B and in a second commercial embodiment, thermal surgical drape 10 would include panel 22 as in FIG. 1B but not chest panel 18 as depicted in FIG. 1A.

The embodiment of FIG. 3 adds parts 34, 36 that overlie the legs of a patient when the legs are required to be separated from one another.

Shield 38 (FIG. 3) is typically a clear plastic piece that protects a patient's face during surgery.

Figure 4A:
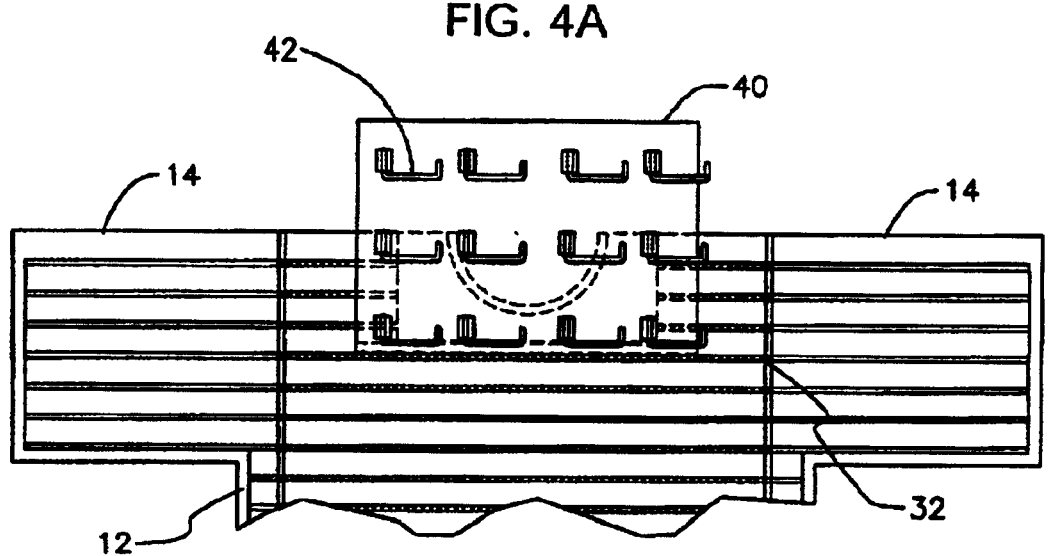
FIG. 4A is a top plan view of an embodiment equipped with a tool-supporting platform, depicting clamps folded into their storage configuration.
Figure 4B:
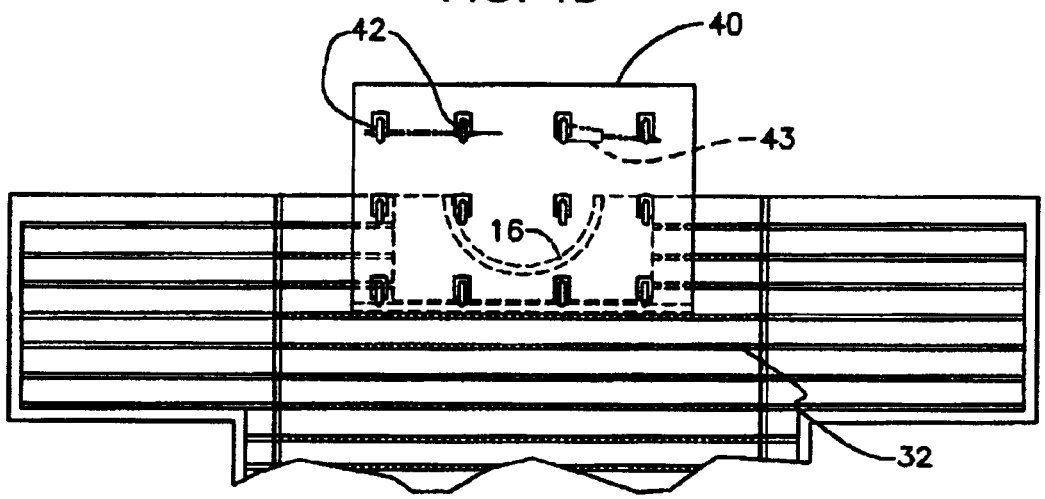
FIG. 4B is a top plan view of the embodiment of FIG. 4A depicting the clamps of the tool-supporting platform in their deployed configuration.

The embodiment of FIGS. 4A and 4B adds a rigid inclined platform 40 that overlies clear plastic face shield 38. A plurality of clamps, collectively denoted 42, are hingedly mounted to platform 40 so that they have a stored position where they lie down flat atop the platform as depicted in the plan view of FIG. 4A and an operable position where they are positioned in upstanding relation to said platform as depicted in FIG. 4B. Note in FIG. 4B that when clamps 42 are deployed, they support various surgical tools 43 and prevent them from rolling down inclined platform 40.

Figure 5:
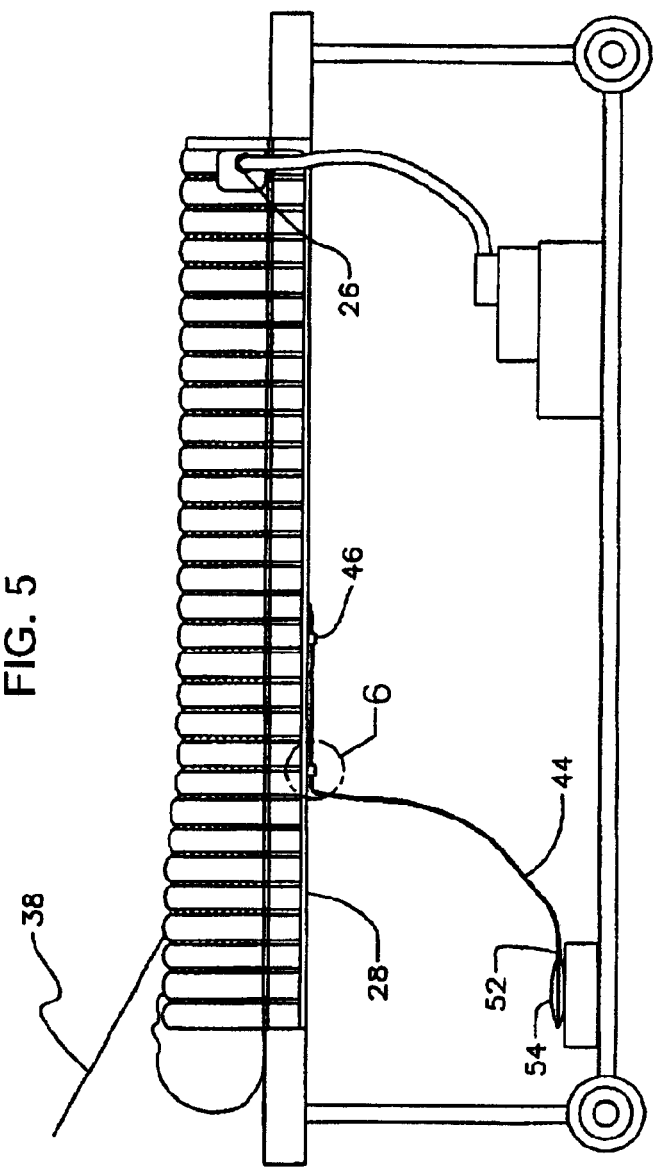
FIG. 5 is a side elevational view of an embodiment that incorporates an elongate bladder tube into the novel structure.
Figure 6:
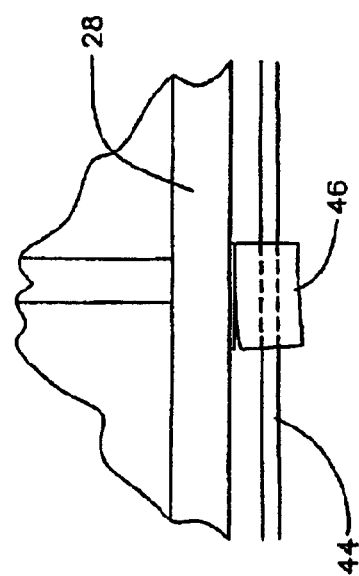
FIG. 6 is an enlarged view of the area denoted 6 in FIG. 5.

FIGS. 5 and 6 depict the means that enable a patient to remain connected to a urine collection bag even after the novel thermal surgical drape has been removed. An elongate tubular member 44 extends through a plurality of support blocks 46 that are detachably secured as best depicted in FIG. 6 to the peripheral edge of substrate 28. A first connector means, not shown, is disposed at a first end of elongate tube 44 and is adapted for releasable engagement with a urine drainage catheter, not shown, that extends from the patient's bladder. A second connector means 52 is disposed at a second end of the elongate tube and is adapted for releasable engagement with urine collection bag 54. When a surgical procedure has been completed, support blocks 46 are separated from substrate 28 in the manner suggested in FIG. 6 so that the first and second connector means remain connected to the unillustrated urine drainage catheter and urine collection bag 54, respectively.

Novel thermal surgical drape 10 thus provides a combined blanket and surgical drape that warms and drapes the entire body of the patient. When fully inflated, tie-downs 32 ensure that it maintains a thin profile as best understood in connection with FIG. 1C. It also provides access to the chest or abdominal area when needed, provides a platform for tools, and enables a patient hooked to a urine collection bag to remain so connected when the thermal surgical drape has been removed upon completion of surgery.

The many advantages of the novel surgical thermal drape are perhaps most appreciated when considered in contrast to a surgical drape of the prior art, denoted 60 as whole in FIG. 7. Warm air is pumped into inlets 26 to maintain warmth in the patient's arms and upper chest. No provision is made for warming the torso or legs of the patient. A separate surgical drape, not shown, must be purchased to cover the balance of the patient's body, but such surgical drapes include no means for warming the torso or the legs of the patient. Moreover, platform 38 includes no means for supporting surgical tools. Novel thermal surgical drape 10 is thus understood to provide the first full body-covering surgical drape where the entire drape is filled with warm air so that the patient's entire body is protected from the chilly environment of a surgery room. A physician using the novel thermal surgical drape therefore needs to purchase only one item instead of a thermal cover for the upper body and a drape for the rest of the body. In addition to the advantages thereby provided, the extra benefits of a tool-supporting platform and a detachable urine tube are also realized.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A combination surgical drape and blanket for patient temperature management, comprising:

a substrate formed of a flexible material;

said substrate having a main body adapted to overlie a patient, said substrate having a width and length sufficient to cover the shoulders, chest, torso, and legs of said patient;

said substrate having a pair of arm-covering members connected to and extending from said main body on opposite sides thereof;

a flexible sheet of material that overlies said substrate;

a plurality of interconnecting members for interconnecting said substrate and said flexible sheet of material, each interconnecting member joining said substrate and said flexible sheet of material together at a point so that said substrate and flexible sheet of material are unconnected to one another around each point;

an air inlet that admits air into a space between said substrate and said flexible sheet of material, said air inlet adapted to admit warm compressed air from a remote source of warm compressed air into said space between said substrate and said flexible sheet of material;

a plurality of small vent holes formed in said flexible sheet of material to enable warm compressed air in said space to exhaust therefrom;

a removably mounted panel formed in said main body, said removably mounted panel including a section of said substrate and said flexible sheet of material bonded to one another at a peripheral edge of said panel so that said panel is not in fluid communication with said inlet means so that when said panel is removed, compressed warm air continues to flow throughout said arm-covering members and all parts of said main body outside the boundary of said removable panel;

whereby said combination surgical drape and blanket performs the function of a surgical drape when disposed in overlying relation to patient;

whereby said combination surgical drape and blanket performs the function of a blanket when warm compressed air is admitted into said space;

whereby removal of said removable panel exposes a part of the patient's body to which access is needed for a surgical procedure.

2. The combination surgical drape and blanket of claim 1, further comprising:

a concavity formed in said main body in a transversely disposed edge thereof, said concavity adapted to receive a patient's head;

a flexible shield of rectangular construction connected at a first edge to said main body and having a second edge opposite to said first edge adapted to be connected to a support means at a point above said patient's head so that said shield is disposed at an angle over said patient's head;

a rigid platform member disposed in overlying relation to said flexible shield;

at least one clamp secured to said platform, said at least one clamp adapted to hold a tool deposited atop said platform;

whereby a tool deposited atop said platform and held by said at least one clamp does not roll down said platform and is therefore available for use.

3. The combination surgical drape and blanket of claim 2, wherein said at least one clamp includes at least one pair of laterally spaced apart clamps so that a first end of a tool is supported by a first clamp of said at least one pair of clamps and so that a second end of said tool is supported by a second clamp of said at least one pair of clamps.

4. The combination surgical drape and blanket of claim 3, wherein each clamp of said at least one pair of laterally spaced apart clamps is hingedly mounted to said rigid platform so that it is storable atop said rigid platform in a folded configuration when not in use and is positioned in upstanding relation to said rigid platform when disposed in an operable configuration.

5. The combination surgical blanket and drape of claim 1, further comprising a pair of bifurcated leg-covering members that extend from said main body, each leg member of said pair of leg members having a structure like that of said main body and said arm-covering members so that the legs of said patient are individually warmed and draped.

6. The combination surgical drape and blanket of claim 1, further comprising: an elongate tube;

a plurality of support blocks arranged along the length of said elongate tube at predetermined intervals, each of said support blocks adapted to receive said elongate tube therethrough;

each of said support blocks being detachably secured to a peripheral edge of said combination surgical drape and blanket;

a first connector means disposed at a first end of said elongate tube, said first connector means adapted for releasable engagement with a distal end of a urine drainage catheter;

a second connector means disposed at a second end of said elongate tube, said second connector means adapted for releasable engagement with a urine collection bag;

whereby when a surgical procedure has been completed, each of said support blocks is separated from said combination surgical drape and blanket;

whereby said first and second connector means remain connected to said urine drainage catheter and said urine collection bag, respectively.

* * * * *